(12) United States Patent
Martin et al.

(10) Patent No.: US 9,557,311 B2
(45) Date of Patent: *Jan. 31, 2017

(54) ELECTROMAGNETIC SPECTRALLY DETECTABLE PLASTIC PACKAGING COMPONENTS

(71) Applicant: ILLINOIS TOOL WORKS, INC., Glenview, IL (US)

(72) Inventors: Robert H. Martin, Gainesville, GA (US); John Gregory Bruce, Lawrenceville, GA (US); Darylnn Phillips Jordan, Lithonia, GA (US); Craig Martin Stearns, Suwanee, GA (US)

(73) Assignee: ILLINOIS TOOL WORKS, INC., Glenview, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/656,234

(22) Filed: Mar. 12, 2015

(65) Prior Publication Data

US 2015/0185195 A1 Jul. 2, 2015

Related U.S. Application Data

(63) Continuation of application No. 13/372,997, filed on Feb. 14, 2012, now Pat. No. 8,980,982.

(60) Provisional application No. 61/467,811, filed on Mar. 25, 2011.

(51) Int. Cl.
| | | |
|---|---|---|
| *G01N 33/20* | (2006.01) | |
| *H01F 1/01* | (2006.01) | |
| *C08K 3/30* | (2006.01) | |
| *C08K 3/04* | (2006.01) | |
| *B29C 45/00* | (2006.01) | |
| *C08K 3/08* | (2006.01) | |
| *B29K 23/00* | (2006.01) | |
| *B29L 31/00* | (2006.01) | |

(52) U.S. Cl.
CPC ........... *G01N 33/20* (2013.01); *B29C 45/0001* (2013.01); *C08K 3/04* (2013.01); *C08K 3/08* (2013.01); *C08K 3/30* (2013.01); *H01F 1/01* (2013.01); *B29K 2023/00* (2013.01); *B29K 2995/0008* (2013.01); *B29L 2031/7142* (2013.01); *C08K 2003/0856* (2013.01); *C08K 2003/3045* (2013.01)

(58) Field of Classification Search
CPC ............ C08L 27/06; C08L 39/00; C08K 3/30; C08K 3/08; C08K 3/04; G01N 33/20
USPC .......................................... 250/200; 524/565
See application file for complete search history.

(56) References Cited

U.S. PATENT DOCUMENTS

| | | |
|---|---|---|
| 3,068,547 A | 12/1962 | L'Hommedieu |
| 3,491,802 A | 1/1970 | Mortensen et al. |
| 3,620,875 A | 11/1971 | Guglieimo, Sr. et al. |
| 3,633,533 A | 1/1972 | Allen et al. |
| 3,756,241 A | 9/1973 | Patience |
| 3,756,512 A | 9/1973 | Dyal |
| 3,867,935 A | 2/1975 | Eisdorfer et al. |
| 3,911,922 A | 10/1975 | Kliger |
| 3,929,659 A | 12/1975 | Graham |
| 4,068,666 A | 1/1978 | Shiff |
| 4,155,487 A | 5/1979 | Blake |
| 4,185,626 A | 1/1980 | Jones et al. |
| 4,345,718 A | 8/1982 | Horvath |
| 4,620,646 A | 11/1986 | Crasper |
| 4,645,499 A | 2/1987 | Rupinskas |
| 4,664,971 A * | 5/1987 | Soens ................... B29C 70/882 174/126.2 |
| 4,692,380 A | 9/1987 | Reid |
| 4,718,897 A | 1/1988 | Elves |
| 4,935,019 A | 6/1990 | Papp, Jr. |
| 4,938,901 A | 7/1990 | Groitzsch et al. |
| 5,045,080 A | 9/1991 | Dyer et al. |
| 5,112,325 A | 5/1992 | Zachry |
| 5,178,354 A | 1/1993 | Engvall |
| 5,379,924 A | 1/1995 | Taylor |
| 5,425,996 A | 6/1995 | Wilkie et al. |
| 5,888,640 A | 3/1999 | Marotta et al. |
| 5,931,824 A | 8/1999 | Stewart et al. |

(Continued)

FOREIGN PATENT DOCUMENTS

| | | |
|---|---|---|
| EP | 1 650 556 A1 | 4/2006 |
| EP | 1650556 | 4/2006 |

(Continued)

*Primary Examiner* — Jim J Seidleck
*Assistant Examiner* — Deve E Valdez
(74) *Attorney, Agent, or Firm* — Avery N. Goldstein; Blue Filament Law PLLC

(57) ABSTRACT

A plastic packaging component is provided that is formed of a resin containing an electromagnetic spectrally detectable additive mixed with the resin. The resin formed into a plastic packaging component of an aerosol package lid, an aerosol spray button, an aerosol spray tube, a trigger sprayer, an integrated lid-sprayer, a grease cartridge, a grease cap, plastic fiber toweling, a packaging strap, a pail lid, a jar cap, or a brush. A process for detecting a displaced packaging component in an organic production stream is provided that includes adding to a resin an electromagnetically detectable additive intermixed with the resin and forming the additive loaded resin into the plastic packaging component. The production stream is then scanned for the detectable signal of the additive. Upon detecting the additive, an alarm signal is provided that the production stream contains the displaced packaging component.

18 Claims, 3 Drawing Sheets

(56) References Cited

U.S. PATENT DOCUMENTS

| | | |
|---|---|---|
| 6,177,113 B1 | 1/2001 | Kress et al. |
| 6,356,782 B1 | 3/2002 | Sirimanne et al. |
| 6,371,904 B1 | 4/2002 | Sirimanne et al. |
| 6,395,147 B1 | 5/2002 | Wheat et al. |
| 6,502,726 B1 | 1/2003 | Yquel |
| D487,353 S | 3/2004 | Wolf |
| 6,825,249 B1 | 11/2004 | Takeda et al. |
| 7,044,957 B2 | 5/2006 | Foerster et al. |
| 7,229,417 B2 | 6/2007 | Foerster et al. |
| 7,465,847 B2 | 12/2008 | Fabian |
| 7,568,590 B1 | 8/2009 | Gross et al. |
| 7,625,397 B2 | 12/2009 | Foerster et al. |
| 7,631,767 B2 | 12/2009 | May et al. |
| 7,668,582 B2 | 2/2010 | Sirimanne et al. |
| 7,703,674 B2 | 4/2010 | Stewart et al. |
| 7,795,491 B2 | 9/2010 | Stewart et al. |
| 8,075,985 B2 | 12/2011 | Lee et al. |
| 2004/0031798 A1 | 2/2004 | Fox et al. |
| 2004/0142495 A1 | 7/2004 | Hartman et al. |
| 2005/0236407 A1 | 10/2005 | Aisenbrey |
| 2007/0205529 A1 | 9/2007 | May et al. |
| 2008/0290649 A1 | 11/2008 | Klein et al. |
| 2010/0124644 A1 | 5/2010 | Hein et al. |

FOREIGN PATENT DOCUMENTS

| | | |
|---|---|---|
| EP | 1 776 006 A1 | 4/2007 |
| EP | 1776006 | 4/2007 |
| GB | 2 315 698 | 2/1998 |
| GB | 2315698 | 2/1998 |
| GB | 2 372 934 A | 9/2002 |
| GB | 2372934 | 11/2002 |
| JP | 2002 020554 | 1/2002 |
| JP | 2002020554 | 1/2002 |
| WO | 9305101 A1 | 3/1993 |
| WO | WO 00/23275 A1 | 4/2000 |
| WO | WO 0023275 | 4/2000 |
| WO | WO 2005/061649 A1 | 7/2005 |
| WO | WO 2005061649 | 7/2005 |
| WO | WO 2006/026823 A1 | 3/2006 |
| WO | WO 2006026823 | 3/2006 |
| WO | WO 2007/012898 | 2/2007 |
| WO | WO 2007012898 | 2/2007 |

* cited by examiner

ELECTROMAGNETIC SPECTRALLY DETECTABLE PLASTIC PACKAGING COMPONENTS

RELATED APPLICATIONS

This application is a continuation of U.S. utility application Ser. No. 13/372,997 filed Feb. 14, 2012; now U.S. Pat. No. 8,980,982; that in turn claims priority benefit of U.S. Provisional Patent Application Ser. No. 61/467,811 filed Mar. 25, 2011; the contents of which are hereby incorporated by reference.

FIELD OF THE INVENTION

The present invention in general relates to industrial material plastic packaging components and in particular, to such plastic components loaded with a substance that renders the resultant plastic component detectable by foreign object detection equipment associated with a product stream.

BACKGROUND OF THE INVENTION

Metal detectors are commonly found on food processing lines to assure that metal shards that represent a laceration hazard do not end up in food products. Similarly, pharmaceutical and biomedical device production are also vulnerable to not only the hazards associated with metal debris ending up in product streams, but also the prospect that such metal can degrade active pharmaceutical ingredients or serve as a potential source of infection. Numerous technologies are known to the art to detect spurious metal within a production line exist. These technologies include a transmitter coil-receiver coils for metal detection systems, systems that use radio frequencies, and magnetic field based systems. In recognition of the fact that some metallic materials are not ferromagnetic and simultaneously not particularly good electrical conductors, x-ray scanners and other electromagnetic field (emf) spectral region spectral detection techniques have been added to food and pharmaceutical product lines to facilitate the detection of a wider range of contaminants.

In spite of the advances in detection of spurious metallic shards in a food or pharmaceutical production line, existing production lines are poorly equipped to detect spurious plastic and other polymeric materials that may enter a food or pharmaceutical production line. This is problematic since such plastic materials not only have the ability to fracture into shards capable of causing a laceration but also with respect to pharmaceutical production, contain organometallic catalysts and plasticizers that can potentially degrade the efficacy of a therapeutic.

Servicing of a food or pharmaceutical production line currently has strict guidelines that require exclusion zones from which various material packaging components are excluded. In spite of these exclusion policies, plastic debris does enter production lines and with even a single piece of plastic entering a production stream, large quantities of otherwise usable product must be discarded. Rules regarding processing of ground meat are exemplary of those that require discard of the product if possibly contaminated. Common plastic packaging that is inadvertently brought into production exclusion zones include aerosol cans, grease cartridge tubes, grease tube caps, plastic fiber toweling, packing straps, pail lids, jar caps, and brushes.

Aerosol cans are routinely used in the food and pharmaceutical production industries to deliver lubricants, sealants and other substances to maintain operation of production equipment. A typical aerosol can is provided with a plastic lid mounted on top of the can to cover the aerosol spray button. To release the pressurized contents of an aerosol can, it is customary to remove the lid, hold the aerosol can in an upright position and depress the aerosol spray button in the intended direction of application. Optionally, a spray tube is joined to the spray button to direct an aerosol spray in a more concentrated pattern from the spray button aperture to the desired target. Such aerosol can lids, spray buttons, and tubes are typically formed through extrusion or injection molding using plastic materials such as polypropylene, acetal, nylon, or high density polyethylene. In using such cans in the context of a food or pharmaceutical industry production line, each of these plastic components of a lid, spray button, and spray tube have the possibility of dislodging from the aerosol can and entering the production stream. Once aerosol packaging components formed of plastic enter such a production stream, there is a limited ability to detect these components or fragments thereof in the course of production.

Thus, there exists a need for a plastic packaging component formed of a substance susceptible to detection by conventional metal detector, X-ray, or other electromagnetic spectral detection techniques to preclude such components from being lost in consumable products streams like those of food or pharmaceutical products.

SUMMARY OF THE INVENTION

A plastic packaging component is provided that is formed of a resin containing an electromagnetic spectrally detectable additive mixed with the resin. The resin formed into a plastic packaging component of an aerosol package lid, an aerosol spray button, an aerosol spray tube, a trigger sprayer, an integrated lid-sprayer, a grease cartridge, a grease cap, plastic fiber toweling, a packaging strap, a pail lid, a jar cap, or a brush.

A process for detecting a displaced packaging component in an organic production stream is provided that includes adding to a resin an electromagnetically detectable additive intermixed with the resin and forming the additive loaded resin into the plastic packaging component such as an aerosol package lid, an aerosol spray button, an aerosol spray tube, a trigger sprayer, an integrated lid-sprayer, a grease cartridge, a grease cap, plastic fiber toweling, a packaging strap, a pail lid, a jar cap, or a brush. The production stream is then scanned for the detectable signal of the additive being present in the product stream. Upon detecting the additive, an alarm signal is provided that the production stream contains the displaced packaging component.

DETAILED DESCRIPTION OF THE PREFERRED EMBODIMENTS

The present invention has utility as plastic packaging component amenable to detection by foreign body detection equipment, especially in the context of an organic substance production stream common to food and pharmaceutical manufacture. Through inclusion of an electromagnetic spectrally detectable loaded plastic resin, it allows for the detection of such components when inadvertently displaced into the organic production stream.

Figure 1:
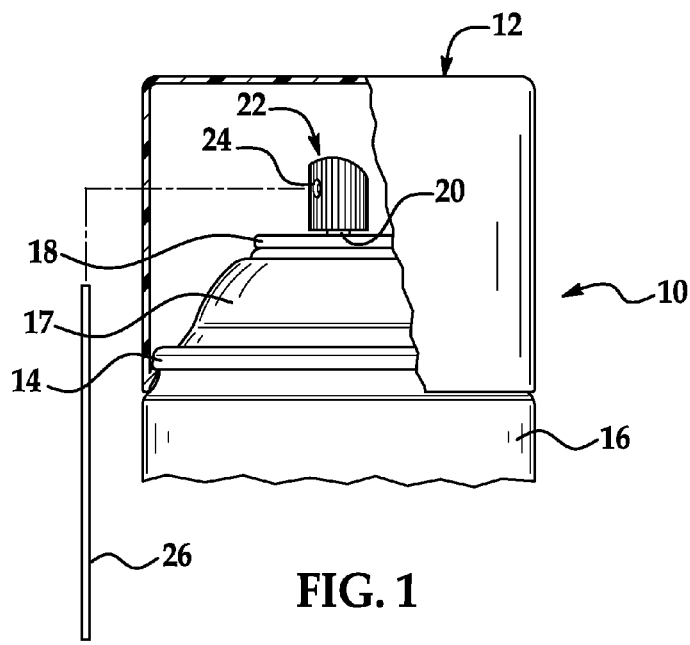
FIG. 1 is a partial cutaway view of an aerosol spray can and of an aerosol spray package depicting various plastic aerosol packaging components formed according to the present invention.

By way of illustration and not intending for it to be bound by the dimensions or structures depicted therein, an aerosol spray can is depicted generally at 10 in FIG. 1 and includes a lid 12 for mounting to a lip 14 surrounding the body 16 or the valve cup 18 of the can 10. A domed closure 17 extends above the lip 14 and terminates in a top rim 18. The top rim 18 having a product release tube 20 extending therefrom encapped with an aerosol spray button 22. The spray button 22 having an aperture 24 therein. The aperture 24 in full communication with the contents of the can 10. An aerosol spray tube 26 is optionally provided to engage the aperture 24 so as to extend therefrom in direct the contents of can 10 through the aperture 24 and through the tube 26 to exit from the distal end thereof.

Figure 2A:
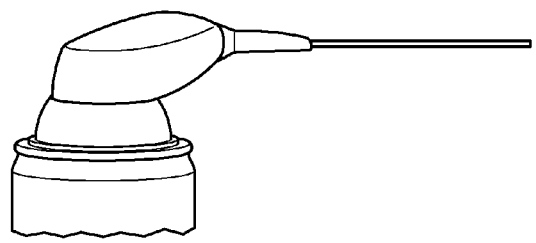
FIGS. 2A-2J are perspective views of various packaging components formed according to the present invention.
Figure 2B:
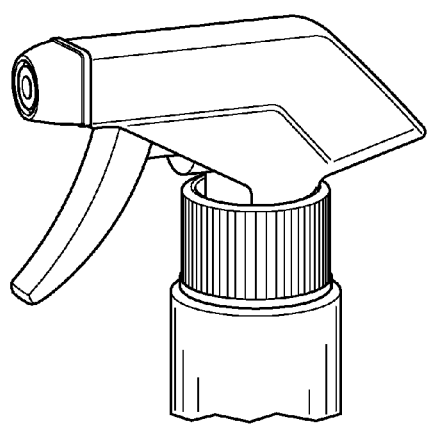
Figure 2C:
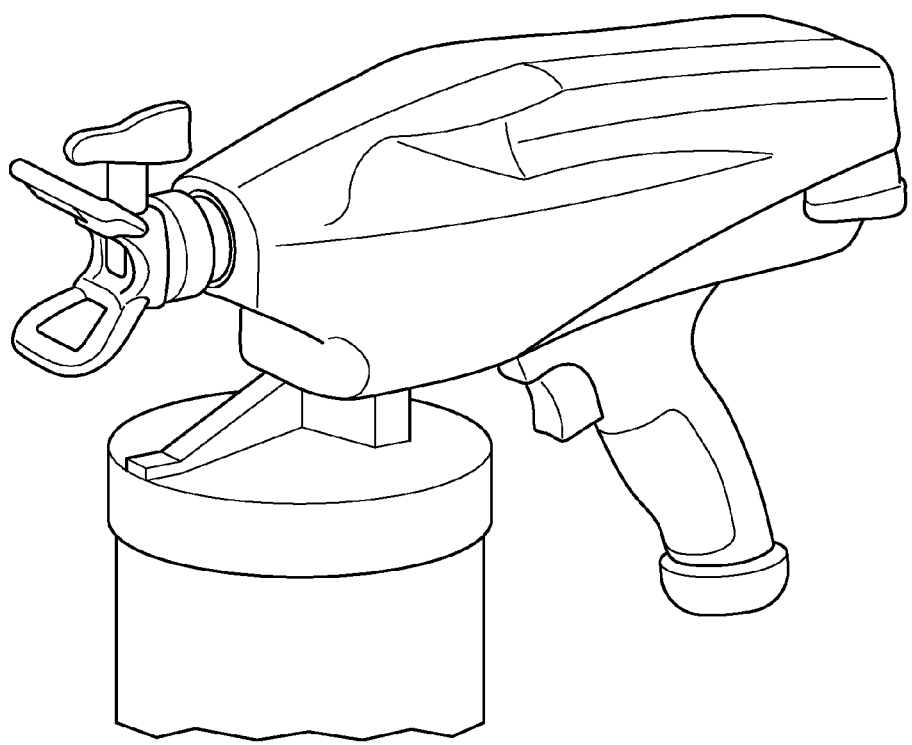
Figure 2D:
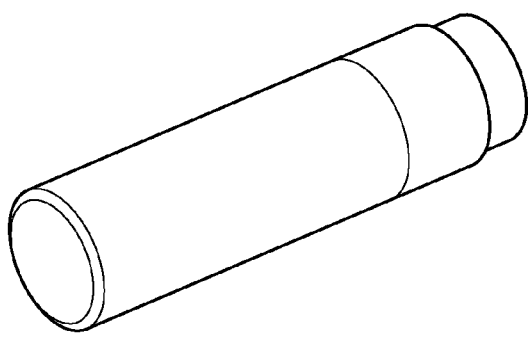
Figure 2E:
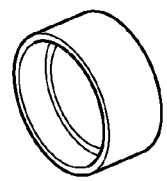

According to the present invention, the plastic aerosol packaging components illustratively including the aerosol package lid 12, the aerosol spray button 22, the aerosol spray tube 26. In addition to those components depicted in FIG. 1 it is appreciated that other aerosol components that are made from an inventive composition illustratively include any plastic aerosol component that has a prospect of detaching from an aerosol application whether pressurized or manually pumped include: clip-on extension tube holder such as that depicted in U.S. Pat. No. 5,178,354; a trigger sprayer such as that depicted in U.S. Pat. Nos. 3,756,512; 4,155,487; and 4,345,718; integrated lid-sprayers such as those depicted in U.S. Pat. Nos. 4,620,646; and 5,379,924; and a combination thereof are formed from conventional thermoplastic resins that are subjected to injection molding or extrusion to form the respective component. Other inventive plastic packaging components are depicted including a clip-on extension tube holder (FIG. 2A), a trigger sprayer (FIG. 2B) and an integrated lid-sprayer (FIG. 2C). Other plastic components that benefit from being detectable and that are common contaminants to food and pharmaceutical production lines are depicted and include a grease cartridge (FIG. 2D), a grease cap (FIG. 2E), a plastic fiber towel sheet (FIG. 2F), a packing strap (FIG. 2G), a pail lid (FIG. 2H), a jar cap (FIG. 2I) and a brush (FIG. 2J). A common feature of inventive components that benefit from electromagnetic spectrally detectable additive inclusion is association with consumable products used to maintain operation of the production line. In certain embodiments, an inventive article is generally not secured to production equipment.

Included in the conventional resin from which a component is formed is an electromagnetically spectrally detectable additive intermixed with the resin. The additive is present in an amount that is detectable by conventional detection techniques common to metal detection, x-ray detection, and microwave detection or other electromagnetic spectral detection techniques. It is appreciated that while these detection techniques may be used in conjunction with imaging the additive or component, the additive detection is not alone based on visible light imaging for locating spurious metallic or high electron density substances in the organic production stream. Such organic production streams are typically associated with the food industry, pharmaceutical industry, animal feedstock industries, and medical products. It is appreciated that such an organic production stream is based largely on carbon containing material, it is recognized that such a stream also contains trace quantities of nutrient metals, organometallic catalysts, metalloenzymes and the like. Shards or pieces of inventive plastic components entering the stream are considered undesirable contaminants and detectable over inherent substance in the product stream.

Resins are from which a plastic aerosol packaging component are formed illustratively include acrylonitrile-butadiene styrene (ABS), acetyl resins, acrylics, ethylene vinyl acetates (EVAs), fluoropolymers, nylons, polycarbonates, polyesters, polyethylenes, polypropylenes, polystyrenes, polyvinyl chlorides, N-vinyl-carpazoles, and polyurethanes, elastomers such as polyisoprene, polybutadiene, polyethylene-polypropylene rubber (EPDM), and styrene-butadiene rubber (SBR); and combinations thereof. Polypropylene and polyethylene represent exemplary thermoplastic resins from which packaging components are molded or extruded. Specifically, high density polyethylene represents a preferred class of polyethylene from which such aerosol packaging components and other packaging components are formed. It is appreciated that an injection moldable composition in addition to the thermoplastic resin also optionally includes plasticizers, colorants, processing aids, fillers such as calcium carbonate, fiberglass, and rutile or other forms of titanium dioxide, and carbon black.

The thermoplastic resin or thermoset resin is intermixed with an electromagnetic spectrally detectable additive, with the additive being present in the resin at a loading and size distribution to facilitate detection. Preferably, the additive is present in a quantity and size that limit the change in processing qualities of the base resin. Typical loadings of such electromagnetic spectrally detectable additives in resin typically range from 1 to 50 total weight percent of the fully loaded resin composition from which an inventive component is formed. In order to prevent the likelihood that the additive will clog or otherwise interfere with resin injection through a molding head, preferably, the additive is in the form of spherical particulate, or at least particulate with an aspect ratio between the longest linear dimension of the particles relative to the shortest linear dimension of the particles of 3:1-1:1.

Preferably, the additive has an average x-y-z linear dimension such that at least 50% of the additive particles present in the plastic resin have an x-y-z average linear dimension of less than 100 microns.

As used herein, "x-y-z average linear dimension" defines the average linear extent of a particle in three orthogonal directions defined by x axis, y axis, and z axis. More preferably, greater than 70% of the additive particles have an average x-y-z linear extent of less than 80 microns. Still more preferably, 90% of the additive particles have an average x-y-z linear extent of less than 50 microns. The additive is optionally pre-coated with one of the aforementioned resins to facilitate dispersion.

The identity of electromagnetic spectrally detectable additives operative herein are largely dictated by compatibility with the resin and susceptibility to detection by the organic production stream detection equipment so employed. Electromagnetic spectrally detectable additives operative herein illustratively include stainless steel, ferrous metals, zinc, aluminum, alloys containing such metals of aluminum, zinc and iron. Barium sulfate and iodine containing compounds represent inorganic, non-metallic, electromagnetic spectrally detectable additive operative herein with a high degree of radio opacity. Typical loadings of such inventive additives commonly range from 1 to 30 total weight percent of the injection moldable resin. Preferably, the additive is selected to be food grade or inert relative to the pharmaceutical or other production stream.

In order to facilitate intermixing of an inventive detectable additive and a thermoplastic resin package suitable for injection molding, preferably, the electromagnetic spectrally detectable additive is intermixed with the thermoplastic resin in concert with a polymercarrier. A suitable polymercarrier is intermixed with the additive to form a pelletized material well suited for intermixing into a screw based thermoplastic extrusion molding machine to form a uniform melt in air mixing with the thermoplastic resin pellets common to the industry. Such pellets are readily formed with a conventional Gala pelletizer. Suitable polymercarriers include the aforementioned thermoplastic resins. Exemplary polymercarriers including polypropylene, ethylene ethyl acrylate, and vinyl acetates. Such polymercarrier intermixed particulate is commercially available from a variety of suppliers including Eriez (Erie, Pa.).

It is appreciated that with the inclusion of the inventive detectable additive, that a degree of embrittlement is often imparted to the resultant component molding relative to such a component formed without such an additive. One of skill in the art will appreciate that one can compensate at least in part for embrittlement through formulation modification such as higher loadings of plasticizers, reduction of conventional fillers within the resin, or resort to a lower glass transition temperature resin.

Figure 2F:
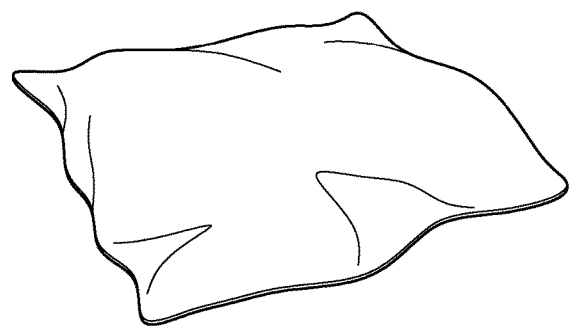
Figure 2G:
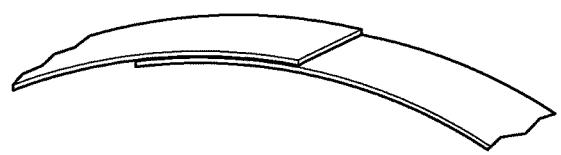
Figure 2H:
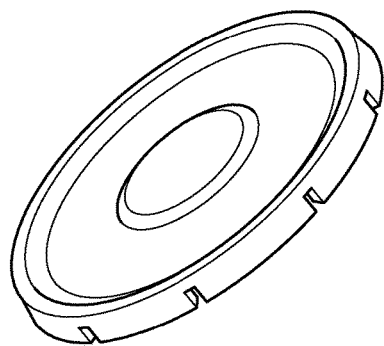
Figure 2I:
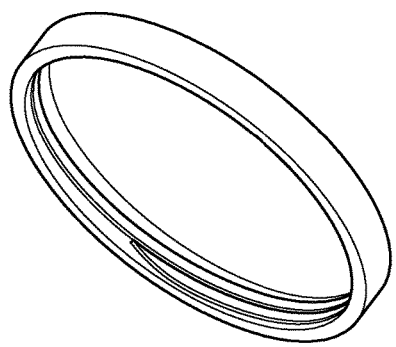
Figure 2J:
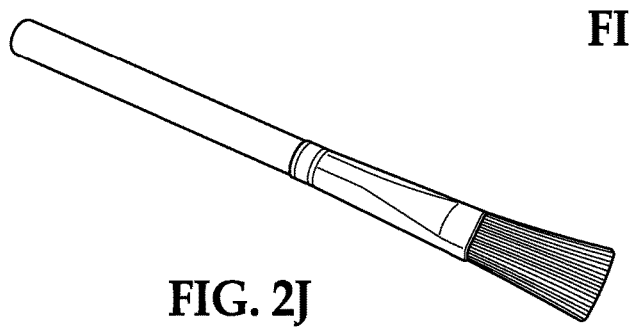

With respect to an inventive plastic towel sheet as depicted in FIG. 2F, a conventional fiber is drawn through a bath containing inventive additive particles so as to render such fibers upon incorporation into a towel sheet electromagnetic spectrally detectable according to the present invention. The fiber is optionally still tacky from production, else the additive is adhered with a conventional contact adhesive or thermoplastic melt. The resultant fiber coated with additive is then used in the manufacture of a plastic fiber towel sheet in the conventional manner.

Upon extrusion, injection molding, or in-mold set of an inventive plastic packaging component, the inventive component is combined with an aerosol package or other container as depicted in FIG. 1 and operates in the same manner as conventional components. However, upon an inventive component being displaced from the package and falling into an organic production stream, such as that associated with food or pharmaceutical production, the production stream is readily scanned for the detectable additive and if found, an alarm is signal. In certain embodiments, upon alarm signaling, the production line is stopped and optionally that portion of the product possibly contaminated is isolated from the pure product. Detection spectroscopies operative herein illustratively include conventional metal detection, x-ray detection, and microwave detection. As a result, displaced components associated with an inventive package are readily detected and removed from the production stream prior to packaging and potential ingestion or other contact by a consumer.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The above description of the present invention should not be construed limiting the scope of the appending claims and instead such description is intended to be exemplary of the present invention. One of ordinary skill in the art will appreciate that variations in modifications exist to the present invention within the scope and spirit of the invention as described and defined in the following claims.

The invention claimed is:

1. A plastic packaging component comprising:
   a thermoplastic or thermoset resin forming a matrix; and
   an-additive of barium sulfate and iodine containing compounds intermixed with said resin, said additive present from 1-50 total weight percent of the component, said additive being food grade or inert relative to a pharmaceutical production stream, said resin formed into a shape of the component; and
   wherein said additive has an average x-y-z linear extent such that at least 50% of additive particles are less than 100 microns, and have an aspect ratio between the longest linear dimension of the particles relative to the shortest linear dimension of the particles of 3:1-1:1.

2. The component of claim 1 wherein the shape is one of an aerosol package lid, an aerosol spray button, an aerosol spray tube, or an aerosol package clip-on extension holder for said tube.

3. The component of claim 1 wherein said resin is one of acrylonitrile-butadiene styrene (ABS), acetyl resins, acrylics, ethylene vinyl acetates (EVAs), fluoropolymers, nylons, polycarbonates, polyesters, polyethylenes, polypropylenes, polystyrenes, polyvinyl chlorides, N-vinyl-carpazole, polyurethanes, polyisoprene, polybutadiene, polyethylene-polypropylene rubber (EPDM), styrene-butadiene rubber (SBR), or combinations thereof.

4. The component of claim 1 wherein said resin is polypropylene.

5. The component of claim 1 wherein said resin is polyethylene.

6. The component of claim 1 wherein said resin is high density polyethylene.

7. The component of claim 1 wherein said additive is barium sulfate.

8. The component of claim 1 wherein said additive is an iodine containing compound.

9. The component of claim 1 wherein said additive has an average x-y-z linear extent such that at least 50% of additive particles are less than 100 microns.

10. The component of claim 1 wherein the shape is a trigger sprayer or an integrated lid sprayer.

11. The component of claim 1 where the shape is a grease cartridge or a grease cap.

12. The component of claim 1 where the shape is a packing strap.

13. The component of claim 1 where the shape is a pail lid or a jar cap.

14. The component of claim 1 further comprising a polymercarrier intermixed with said additive prior to said additive being intermixed with said resin.

15. A plastic packaging component comprising:
   a thermoplastic or thermoset resin forming a matrix; and
   an-additive of stainless steel intermixed with said resin, said additive present from 1-50 total weight percent of the component, said additive being food grade or inert relative to a pharmaceutical production stream, said resin formed into a shape of the component; and
   wherein said additive has an average x-y-z linear extent such that at least 50% of additive particles are less than 100 microns, and have an aspect ratio between the longest linear dimension of the particles relative to the shortest linear dimension of the particles of 3:1-1:1 and formed into an article having a shape of one of: an integrated lid sprayer, an aerosol package lid, an aerosol spray tube, an aerosol package clip-on extension holder for said tube, grease cartridge, a grease cap, a packing strap, a pail lid, a jar cap or a brush.

16. A plastic packaging component comprising:
a thermoplastic or thermoset resin forming a matrix; and
an-additive of stainless steel intermixed with said resin, said additive present from 1-50 total weight percent of the component, said additive being food grade or inert relative to a pharmaceutical production stream, said resin formed into a shape of the component; and
wherein said additive has an average x-y-z linear extent such that at least 50% of additive particles are less than 100 microns, and have an aspect ratio between the longest linear dimension of the particles relative to the shortest linear dimension of the particles of 3:1-1:1 and formed into an article, wherein said article is a plastic fiber towel sheet.

17. A plastic packaging component comprising:
a thermoplastic or thermoset resin forming a matrix; and
an-additive of stainless steel intermixed with said resin, said additive present from 1-50 total weight percent of the component, said additive being food grade or inert relative to a pharmaceutical production stream, said resin formed into a shape of the component; and
wherein said additive has an average x-y-z linear extent such that at least 50% of additive particles are less than 100 microns, and have an aspect ratio between the longest linear dimension of the particles relative to the shortest linear dimension of the particles of 3:1-1:1 and formed into an article, wherein said article is a trigger sprayer.

18. A plastic packaging component comprising:
a thermoplastic or thermoset resin forming a matrix; and
an-additive of stainless steel intermixed with said resin, said additive present from 1-50 total weight percent of the component, said additive being food grade or inert relative to a pharmaceutical production stream, said resin formed into a shape of the component; and
wherein said additive has an average x-y-z linear extent such that at least 50% of additive particles are less than 100 microns, and have an aspect ratio between the longest linear dimension of the particles relative to the shortest linear dimension of the particles of 3:1-1:1 and formed into an article, wherein said article is an aerosol spray button.

\* \* \* \* \*